United States Patent [19]

McPhee

[11] Patent Number: 4,675,020

[45] Date of Patent: Jun. 23, 1987

[54] CONNECTOR

[75] Inventor: Charles J. McPhee, Huntington Beach, Calif.

[73] Assignee: Kendall McGaw Laboratories, Inc., Irvine, Calif.

[21] Appl. No.: 785,789

[22] Filed: Oct. 9, 1985

[51] Int. Cl.[4] ............................................ A61M 5/00

[52] U.S. Cl. .................................. 604/411; 604/414; 604/240

[58] Field of Search ........................ 604/411, 413-415, 604/410, 240

[56] References Cited

U.S. PATENT DOCUMENTS

| | | | |
|---|---|---|---|
| Re. 29,656 | 6/1978 | Chittenden et al. . | |
| 3,872,867 | 3/1975 | Killinger | 604/413 |
| 3,882,909 | 5/1975 | Ogle | 604/413 |
| 3,999,543 | 12/1976 | Lacey . | |
| 4,059,112 | 11/1977 | Tischlinger . | |
| 4,128,098 | 12/1978 | Bloom et al. . | |
| 4,161,178 | 7/1979 | Genese . | |
| 4,169,475 | 10/1979 | Genese . | |
| 4,191,225 | 3/1980 | Ogle . | |
| 4,201,208 | 5/1980 | Cambio, Jr. . | |
| 4,203,443 | 5/1980 | Genese . | |
| 4,346,820 | 8/1982 | Cavazza . | |
| 4,364,387 | 12/1982 | Larkin . | |
| 4,410,321 | 10/1983 | Pearson et al. . | |
| 4,411,661 | 10/1983 | Kersten . | |
| 4,411,662 | 10/1983 | Pearson . | |
| 4,432,755 | 2/1984 | Pearson . | |
| 4,432,765 | 2/1984 | Oscarsson . | |
| 4,458,733 | 7/1984 | Lyons . | |
| 4,467,588 | 8/1984 | Carveth . | |
| 4,568,336 | 2/1986 | Cooper | 604/413 |

FOREIGN PATENT DOCUMENTS

| | | |
|---|---|---|
| US80/01336 | 10/1080 | PCT Int'l Appl. . |
| 2105695 | 7/1982 | United Kingdom . |

OTHER PUBLICATIONS

"Coming From Abbott", The ADD-Vantage System, Abbott Laboratories, 97/1923/R3-2.5-May 1985.

*Primary Examiner*—C. Fred Rosenbaum
*Assistant Examiner*—Sherri E. Vinyard
*Attorney, Agent, or Firm*—John A. Kane

[57] ABSTRACT

A connector including a base and first and second tubular members projecting in generally opposite directions from the base. Each of the tubular members has a longitudinal passage therein, and the passages are communicable with each other. The base can be coupled to first and second containers to place the first and second tubular members within the first and second containers, respectively, so that communication between the containers can be established. The connector includes a plurality of pointed projections extending away from the base to accommodate certain production tolerances in the containers.

7 Claims, 6 Drawing Figures

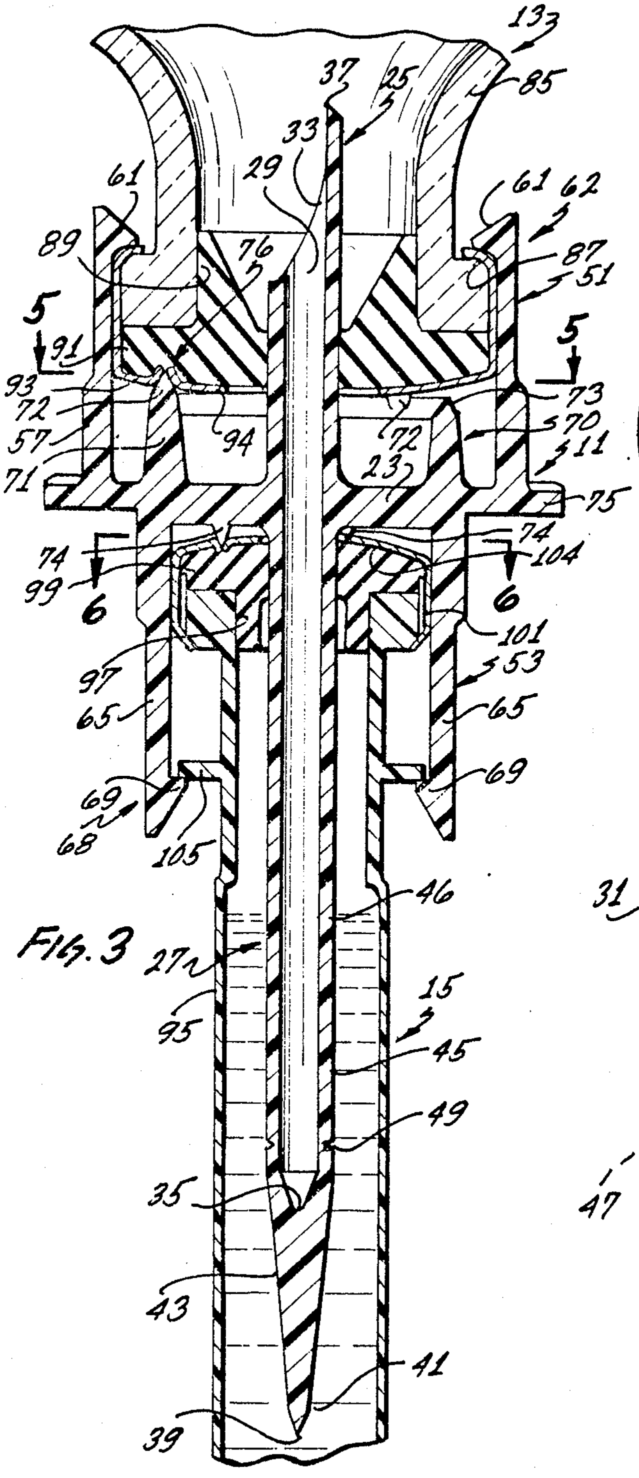
FIG. 3
FIG. 6
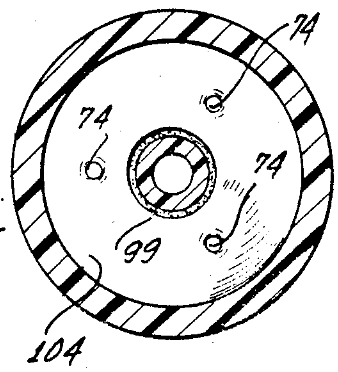
FIG. 4
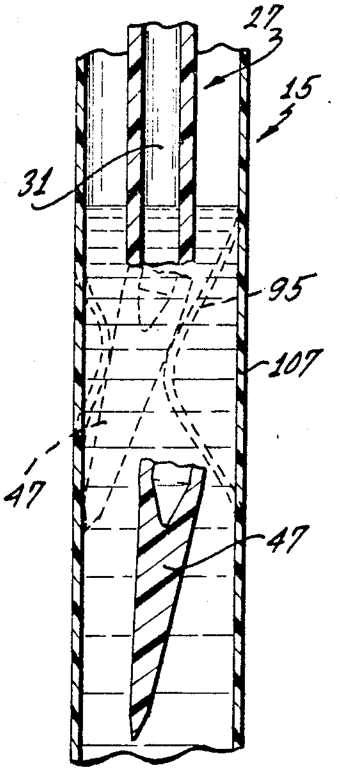

CONNECTOR

BACKGROUND OF THE INVENTION

Various liquids, such as drugs and diluents, are provided in sealed containers. The closures for these containers are, in many cases, penetrable so that a spiked member can be forced through the closure to provide access to the contents of the container.

In some instances, it is necessary or desirable to firmly attach a spiked apparatus to a container for a medical liquid. The connector or binary adapter shown in my copending application Ser. No. 785,835 entitled binary adapter filed on even date herewith is one example of this kind of spiked apparatus.

A container of the type referred to above typically has a relatively deformable end surface which is provided, at least in part, by the penetrable closure and a shoulder axially inwardly of the end surface. A connector or other apparatus can be attached to such a container by gripping the container between the shoulder and the end surface. One problem with gripping the container in this manner is that the distance between the shoulder and the end surface is subject to variations from container to container as a result of production tolerances. The connector or other apparatus which is to be attached to the container is typically an inexpensive molded component which has no means to accommodate such variations. Consequently, in some instances, the connector may not be securely attached to the container, and in other instances, it may be difficult or impossible to attach the connector to the container.

SUMMARY OF THE INVENTION

This invention eliminates the problems described above. With this invention, the deformable nature of the end surface of the container is used to compensate for variations in the distance between the shoulder and the end surface. This is accomplished by providing at least one pointed projection which can dig into or deform the deformable end surface, and by doing this in accordance with this invention, production tolerances can be accommodated.

The features of this invention are adapted for use with virtually any apparatus that is to be attached to a container of this type. For example, the apparatus may be a connector for coupling a container to another member, such as a second container, or an apparatus for gaining access to the liquid within the container.

With this invention, the shoulder and the end surface are held between first and second jaws, and the second jaw terminates in at least one relatively sharp point. The relatively sharp point digs into and deforms the deformable end surface sufficiently to accommodate the dimensional variations of the container. With this construction, a simple, inexpensive apparatus having no moving parts can be firmly attached to containers of this type notwithstanding the dimensional variations. An additional advantage of the sharp point is that it indents the end surface to provide an indicia of use of, or tampering with, the container.

More specifically, in a preferred construction, the apparatus includes a base and a resilient coupling member projecting from the base and adapted to receive the region of the container adjacent the shoulder. The coupling member has the first jaw, and the first jaw extends radially inwardly in spaced relationship to the base for engaging the shoulder and retaining the container against movement away from the apparatus. The second jaw is provided on the base radially inwardly of the coupling member and projects from the base in the same direction as the coupling member. The relatively sharp point terminates proximally of the first jaw.

Preferably, there are a plurality of the relatively sharp points on the second jaw. For greater stability, at least three of the points should be provided, and these points should be circumferentially spaced with equal spacing being preferred. The second jaw may include pointed projections which terminate in sharp points and project directly from the base. Alternatively, the second jaw may include an appropriate raised section and pointed projections on the raised section to accommodate a container of a particular construction.

The resilient coupling member can be of any type that will adequately cooperate with the shoulder of the container. For example, the resilient coupling member may include a resilient segmented skirt.

The apparatus may be used in association with one or more tubular members which project from the base, and any desired number of the tubular members may terminate in a pointed distal end so as to form a spike. For example, a tubular member may project from the base radially inwardly of the coupling member and be adapted to extend into the container when the apparatus is attached to the container. Alternatively or in addition thereto, a tubular member may project from the base in a direction generally opposite the direction in which the coupling member projects from the base. In the latter event, the apparatus may include means coupled to the base for use in coupling the base to a second container. The tubular members may be used, for example, to drain liquid from one of the containers or to mix the liquids in the two containers. Although the apparatus is particularly adapted for use with medical liquids, it is more generally applicable to containers carrying any flowable material.

The invention, together with additional features and advantages thereof, may best be understood by reference to the following description taken in connection with the accompanying illustrative drawing.

BRIEF DESCRIPTION OF THE DRAWING

FIG. 3 is an enlarged, fragmentary sectional view taken on an axial plane through the assembled drug vial, connector and diluent container prior to the removal of the removable section of the tubular member.

FIG. 4 is a fragmentary sectional view taken on an axial plane illustrating the removal of the removable section.

FIGS. 5 and 6 are sectional views taken generally along lines 5—5 and 6—6, respectively, of FIG. 3.

DESCRIPTION OF THE PREFERRED EMBODIMENTS

Figure 1:
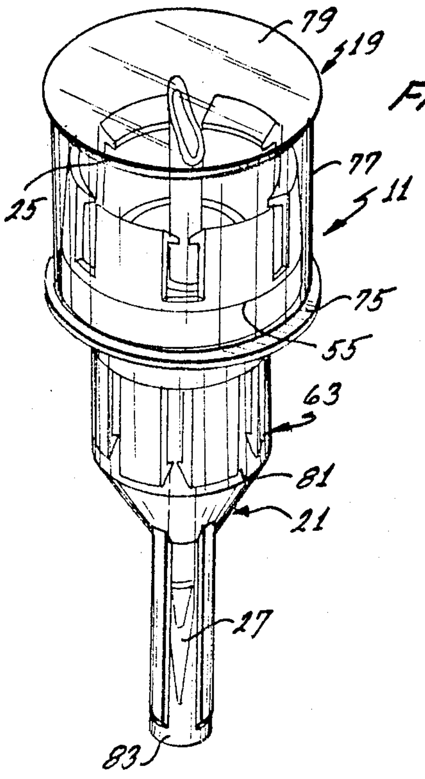
FIG. 1 is an isometric view of a connector constructed in accordance with the teachings of this invention.
Figure 2:
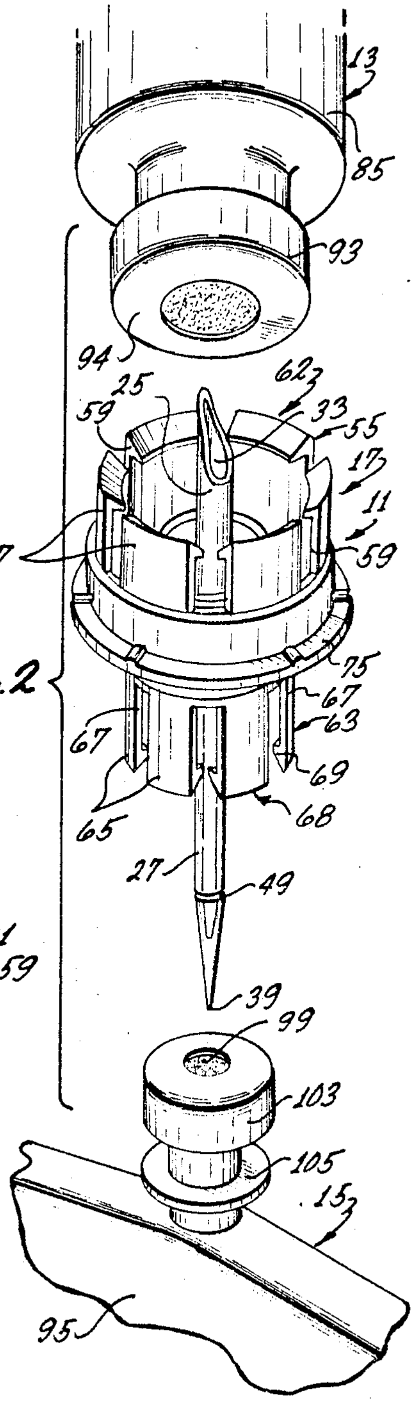
FIG. 2 is an exploded, fragmentary isometric view of the connector with the guard covers removed and of portions of a drug vial and diluent container.
Figure 5:
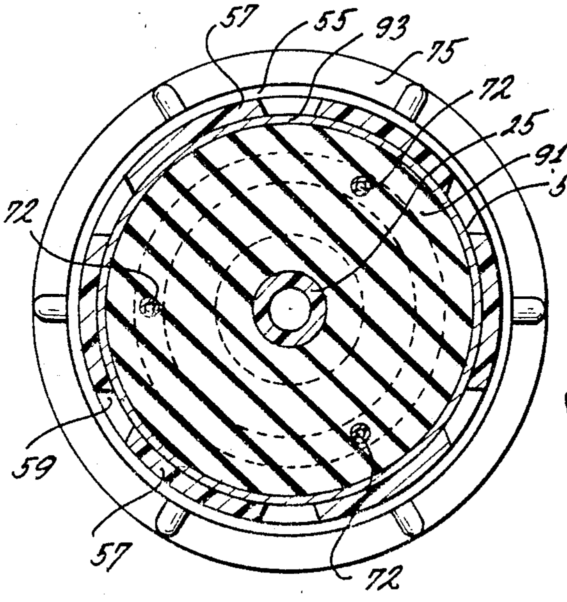

FIG. 1 shows a connector 11 for use in joining and selectively providing communication between a standard container or drug vial 13 and a standard diluent container 15 as shown in FIGS. 2 and 3. The connector 11 comprises a main body 17 and may be considered as including, or being usable with, hollow, semi-transparent guard covers 19 and 21.

The main body 17 is preferably integrally molded from a suitable plastic material, such as polycarbonate, and includes a base 23 (FIG. 3), a tubular member in the form of a drug spike 25 and a tubular member in the form of a diluent spike 27. The spikes 25 and 27 project in opposite directions from the base 23 and have longitudinally extending, coaxial passages 29 and 31, respectively, therein which communicate through the base 23. Accordingly, the passages 29 and 31 may be considered as a single passage which extends from an opening 33 at the distal end of the drug spike 25 continuously and axially through the drug spike 25, the base 23 and to a wall 35 of the diluent spike 27. The wall 35 closes the passage 31 at a distal location, and the passage 31 is open at a proximal location. Spikes 25 and 27 terminate distally in points 37 and 39, respectively.

The point 39 is defined by a conical surface 41 which has its apex substantially at the point 39. A conical surface 43 extends from the proximal end of the conical surface 41 proximally for a relatively long distance and merges with a cylindrical, peripheral surface 45 of the spike 27. As shown in FIG. 3, the cone or apex angle of the conical surface 41 is greater than the corresponding angle of the conical surface 43. This characteristic provides the spike 27 with substantial strength and also a relatively sharp point 39 for puncturing purposes as described more fully hereinbelow. In addition, the spike 27 is solid within essentially all of the conical surfaces 41 and 43, i.e., the passage 31, terminates near the proximal end of the conical surface 43, and this imparts further strength to this region of the spike 27.

The diluent spike 27 has a proximal section 46 and a removable section 47. In this embodiment, the removable section is defined by a line of weakness in the form of a scoreline 49 which extends 360 degrees around the cylindrical peripheral surface 45 just proximally of the wall 35. Thus, the removable section 47 includes an entire distal region of the spike 27, including the wall 35 and the point 39.

The main body 17 also includes a first coupling or coupling means 51 for use in coupling the base and entire main body 17 to the drug vial 13, and a second coupling or coupling means 53 for use in coupling the base and the entire main body to the diluent container 15. The couplings 51 and 53 can be of various different configurations. In the illustrated embodiment, the coupling 51 comprises a generally cylindrical skirt or coupling member 55 segmented into a plurality of axially extending, resilient skirt sections 57 by circumferentially spaced, axially extending slots 59. As best seen in FIG. 3, the skirt 55 projects axially from the base 23 along the spike 25, and each of the skirt sections 57 terminates in a radially inwardly extending flange 61. Collectively, the flanges 61 form a jaw 62.

Similarly, the coupling 53 comprises a generally cylindrical skirt or coupling member 63 segmented into a plurality of axially extending, resilient skirt sections 65 by circumferentially spaced, axially extending slots 67. The skirt 63 projects axially from the base 23 along the diluent spike 27 coaxial with the skirt 55 and has a smaller diameter than the skirt 55. Each of the skirt sections 65 terminates in a radially, inwardly extending flange 69. Collectively, the flanges 69 form a jaw 68 (FIG. 3).

The coupling 51 also includes a second jaw 70 on the base 23 radially inwardly of the skirt 55 and projecting from the base in the same direction as the skirt 55. Although the jaw 70 could be of various different configurations, in the embodiment illustrated, it includes a cylindrical raised section or inner skirt 71 (FIG. 3) which projects from the base 23 and extends along the spike 25 and three pointed projections 72. More specifically, the skirt 71 terminates distally in the pointed projections 72 with such projections extending axially from an edge 73 of the skirt. In this embodiment, the skirt 71 is coaxial with the spike 25 and is surrounded by the skirt 55. Although various arrangements can be employed, in the embodiment illustrated, the pointed projections 72 are equally spaced circumferentially and are equally spaced from the axis of the skirt 71. As shown in FIG. 6, each of the pointed projections 72 extends distally beyond the edge 73 for a short distance and is of generally conical shape so as to terminate in a sharp point.

The coupling 53 also includes a second jaw 76 on the base 23 radially inwardly of the skirt 63 and projecting from the base in the same direction as the skirt 63. The second 76 jaw includes three pointed projections 74, each of which terminates proximally of the flanges 69 in a sharp point. The pointed projections 74 in this embodiment are conical, equally spaced circumferentially from each other and equally spaced radially from the axis of the spike 27. The pointed projections 74 are much like the pointed projections 72, except they are not spaced from the base 23 by a skirt, and in this embodiment, they are closer to the axis of the spike 27. The main body 17 also has an annular flange 75 surrounding the skirt 55 and projecting radially outwardly therefrom.

The guard covers 19 and 21 are provided for protecting the user against injury from the spikes 25 and 27, respectively. Although each of the guard covers 19 and 21 could be of various different constructions, in the embodiment illustrated, the guard cover 19 has a generally cylindrical peripheral wall 77, a generally circular end wall 79 and an open end opposite the end wall 79. The peripheral wall 77 is sized to be slid over the skirt 55 with a friction fit as shown in FIG. 1 to protect the user against the spike 25.

Similarly, the guard cover 21 has a peripheral wall 81 which is tailored somewhat to the configuration of the skirt 63 and the spike 27, an end wall 83 and an open end opposite the end wall 83. The peripheral wall 81 can be slid over the skirt 63 with a friction fit to protect the user from injury from the spike 27 as shown in FIG. 1.

In the position shown in FIG. 1, the guard covers 19 and 21 engage the opposite faces of the flange 75, and the flange 75 projects radially outwardly of the guard covers between the guard covers. With this construction, the user can grasp the periphery of the flange 75 with one hand and remove either the guard cover 19 or the guard cover 21 without removing the other guard cover. This enables the user to select which of the guard covers will be removed and minimizes the likelihood of injury in the guard cover removal process. Ordinarily, it will be desired to remove the guard cover 19 first.

The connector 11 in the embodiment illustrated can be coupled to a standard 20 millimeter drug vial, such as the drug vial 13, and to a diluent container of the type manufactured by American Hospital Supply Corporation, such as the diluent container 15. The vial 13 is in the form of a bottle 85 having an annular shoulder 87 (FIG. 3) surrounding an opening 89 of the bottle. The opening 89 is sealed by a deformable and penetrable rubber stopper 91 which is covered by an apertured cap 93 of a soft metal, such as aluminum. The cap 93 cooperates with the stopper to provide a deformable end surface 94.

When the connector 11 is attached to the drug vial 13, it grips the drug vial between the shoulder 87 and the deformable surface 94 as described more particularly hereinbelow. Unfortunately, the distance between the shoulder 87 and the end surface 94 inherently varies from container to container due to production tolerances. The connector 11, being an inexpensive part molded of plastic material, has no adjustable jaws or clamping members to accommodate the production tolerances of the drug vial. However, with this invention, the pointed projections 72 deform the deformable surface 74 of the drug vial 13 sufficiently to accommodate the variations in the distance between the shoulder 87 and the end surface 94.

More specifically, with the guard cover 19 removed, the spike 25 can be forced through the stopper 91 to the position shown in FIG. 3 in which the passage 29 communicates with the interior of the bottle 85 so that it can receive a drug in liquid form from the bottle. Mechanically, the region of the drug vial 13 between the shoulder 87 and the deformable end surface 94 is gripped between the jaws 62 and 70, i.e., the pointed projections 72 to firmly retain the connector on the drug vial. The skirt sections 57 are sufficiently resilient to permit them to flex radially outwardly to allow advancing the drug vial 13 and the connector 11 to the position shown in FIG. 3.

The pointed projections 72 deform the deformable surface 94 and dig into it and into the stopper 91 to accommodate production tolerances. In this regard, the distance between the jaws 62 and 70 is small enough to allow the pointed projections 72 to dig into the end surface 94 of the drug vial having the minimum anticipated distance between the shoulder 87 and the end surface 94. The three pointed projections 72 form a plane which stably supports the drug vial 13. Moreover, if the connector 11 should ever become separated from the drug vial 13, the indentations in the end surface 94 formed by the pointed projections 72 constitute indicia of use of, or tampering with, the drug vial so that it should not be reused.

With the connector 11 attached to the drug vial 13, the drug vial 13 can be used as a handle for the connector 11. By grasping the drug vial 13, the guard cover 21 can then be removed from the main body 17.

The container 15 is in the form of a flexible bag having a flexible wall 95. The container 15 has an opening 97 (FIG. 3) which is sealed by a deformable and penetrable rubber stopper 99 and covered by an inner cap 101 of a soft metal, such as aluminum, and an outer removable cap 103 (FIG. 2) of plastic. The cap 101 cooperates with the stopper 99 to provide a deformable end surface 104. Typically, the container 15 will have a second opening (not shown) which is closed in the same manner as the opening 97. The container 15 has an annular flange 105 just below cap 103, and the container has a suitable diluent 107 therein.

With the guard cover 21 and the outer cap 103 removed and, with the vial 13 attached to the connector 11 as shown in FIG. 3, the vial can be used as a handle, and the spike 27 forced through the stopper 99 into the interior of the container 15. Coupling of the connector 11 to the container 15 is accomplished by gripping of the shoulder 105 and the deformable end surface 104 between the jaws 68 and 76, i.e., and the pointed projections 74. The skirt sections 65 can flex sufficiently to permit locking engagement of the jaw 68 with the flange 105.

The distance between the shoulder 105 and the end surface 104 is subject to variations due to production tolerances. However, because the pointed projections 74 can dig into and deform the deformable end surface 104, these tolerance variations can be accommodated without providing adjustable parts on the connector 11. The distance between the jaw 69 and the pointed projections 74 is established so that the pointed projections 74 will deform the end surface of the container 15 having the largest anticipated distance between the shoulder 105 and its end surface 104. Thus, both halves of the connector 11 function in virtually identical fashion to attach the connector to the associated container while accommodating certain dimensional variations without employing moving parts.

With the components in the position of FIG. 3, drug from the vial 13 can enter the passage 29 and flow into the passage 31. However, because the passage 31 is a blind or closed passage, the diluent 107 in the container 15 cannot mix with the drug.

When it is desired to use the drug, the removable section 47 is broken off of the remainder of the spike 27 by applying a bending force to the spike 27 as shown in FIG. 4 to open the distal end of the passage 31 to permit the diluent 107 to mix with the drug from the vial 13. The flexible wall 95 can be flexed or manipulated as necessary to enable an appropriate bending force to be applied to break off the removable section 47 along the scoreline 49. The breaking of the removable section 47 is accomplished without the need for any special plunger or other actuating member. Once communication is established between the drug vial 13 and the interior of the container 15 through the passages 29 and 31, the container 15 can be pumped or milked as necessary to provide thorough mixing of the drug and diluent.

The connectors 11 can be provided separately to hospitals and pharmacies for use as needed with drug vials 13 and diluent containers 15. Alternatively, the connector 11 can be preassembled onto each drug vial 13 and furnished in this manner to the using facility. In this event, it may be desirable to employ a different form of connector-to-vial connection, and the spike 25 may be eliminated in favor of any passage that will provide communication to the passage 31 of the spike 27. Finally, the connector 11 and the container 15, with or without the drug vial 13, may be preassembled at the factory and furnished in assembled condition to the using facility. In this event, the spike 27 could be eliminated in favor of a blunt tubular member with a blind bore and a removable section.

Although the features of this invention relating to the accommodation of dimensional variations is illustrated and described with reference to a connector having a frangible spike, it is, of course, more broadly applicable to the attachment of various apparatuses to containers subject to this dimensional variation. Although exemplary embodiments of the invention have been shown and described, many changes, modifications and substitutions may be made by one having ordinary skill in the art without necessarily departing from the spirit and scope of this invention.

I claim:

1. An apparatus attachable to a container with an opening which container has penetrable stopper means and an apertured cap for securing said stopper means within said opening, said cap having a relatively deformable outer end surface and a shoulder inwardly of the end surface and with the distance between the shoulder and the end surface being subject to variations, said apparatus comprising:

a base;

a resilient coupling member projecting from the base and adapted to receive the region of the container adjacent the shoulder; said coupling member having a first jaw extending radially inwardly in spaced relationship to the base for engaging the shoulder and retaining the container against movement away from the apparatus;

a second jaw on said base radially inwardly of the coupling member; and said second jaw terminating proximally of the first jaw in at least one relatively sharp point which is positioned to contact said outer end surface of said cap when said apparatus is attached to said container whereby the region of the container between the shoulder and the end surface of said cap can be gripped between the jaws to retain the connector on the container with the relatively sharp point deforming the deformable surface of the container sufficiently to accommodate variations in the distance between the shoulder and the end surface of the cap.

2. An apparatus as defined in claim 1 wherein said second jaw terminates proximally of the first jaw in at least three of said relatively sharp points.

3. An apparatus as defined in claim 1 wherein said second jaw terminates proximally of the first jaw in a plurality of substantially equally spaced relatively sharp points.

4. An apparatus as defined in claim 1 wherein said second jaw includes a raised section terminating distally in said relatively sharp point.

5. An apparatus as defined in claim 1 wherein said coupling member includes an outer segmented skirt and said second jaw includes an inner skirt terminating distally in a plurality of said relatively sharp points.

6. An apparatus as defined in claim 1 including a tubular member projecting from said base in the same general direction as the coupling member, said tubular member lying radially inwardly of the coupling member and being adapted to project into the container when the apparatus is attached to the container.

7. An apparatus as defined in claim 1 including a tubular member projecting from the base in a direction generally opposite to the direction in which the coupling member projects from the base and a second coupling member for use in coupling the base to a second container with the tubular member projecting into the second container.

* * * * *